(12) United States Patent
Machida et al.

(10) Patent No.: US 7,198,906 B2
(45) Date of Patent: Apr. 3, 2007

(54) DRUG SENSITIVITY MEASURING METHOD

(75) Inventors: Katsuhiko Machida, Tokyo (JP); Sadayori Hoshina, Tokyo (JP); Takashi Ushida, Ibaraki (JP); Junichiro Arai, Ibaraki (JP); Hideo Katayama, Ibaraki (JP); Chiaki Okumura, Ibaraki (JP); Yoshihisa Amano, Ibaraki (JP)

(73) Assignees: Jikei University School of Medicine, Tokyo (JP); Japan as Represented by Director-General of National Institute of Advanced Industrial Science and Technology, Ministry of Economy, Trade and Industry, Tokyo (JP); Daikin Industries, Ltd., Osaka (JP)

( * ) Notice: Subject to any disclaimer, the term of this patent is extended or adjusted under 35 U.S.C. 154(b) by 344 days.

(21) Appl. No.: 10/221,800

(22) PCT Filed: Mar. 19, 2001

(86) PCT No.: PCT/JP01/02198

§ 371 (c)(1), (2), (4) Date: Jan. 2, 2003

(87) PCT Pub. No.: WO01/68905

PCT Pub. Date: Sep. 20, 2001

(65) Prior Publication Data

US 2003/0180831 A1 Sep. 25, 2003

(30) Foreign Application Priority Data

Mar. 17, 2000 (JP) ............................... 2000-081765

(51) Int. Cl.
*C12Q 1/18* (2006.01)
*C12M 1/34* (2006.01)

(52) U.S. Cl. ..................................... 435/32; 435/287.1
(58) Field of Classification Search ..................... None
See application file for complete search history.

(56) References Cited

U.S. PATENT DOCUMENTS

| 4,009,078 A | | 2/1977 | Wilkins et al. |
| 4,209,586 A | * | 6/1980 | Noller .......................... 435/32 |
| 4,311,794 A | | 1/1982 | Melnick et al. |
| 4,321,322 A | | 3/1982 | Ahnell |
| 5,654,165 A | | 8/1997 | Kusunoki et al. |
| 5,876,959 A | | 3/1999 | Kusunoki et al. |
| 6,143,555 A | | 11/2000 | Kusunoki et al. |

FOREIGN PATENT DOCUMENTS

| EP | 0 128 527 | 12/1984 |
| EP | 0 609 458 | 8/1994 |
| EP | 0 632 131 | 1/1995 |
| JP | 10-276795 | 10/1998 |

OTHER PUBLICATIONS

Abu-Amero et al. (Applied and Environmental Microbiology, vol. 62, No. 9, pp. 3107-3111).*
Wodnicka et al. Journal of Biomolecular Screening, 2000. vol. 5, No. 3, pp. 141-152.*

* cited by examiner

*Primary Examiner*—Jon Weber
*Assistant Examiner*—Kailash Srivastava
(74) *Attorney, Agent, or Firm*—Smith, Gambrell & Russell, LLP

(57) ABSTRACT

Disclosed herein is a method for determining the drug sensitivity of a microbe which comprises pouring a microbial suspension into each of the compartments or wells at a position which is in the vicinity of an electrode for measuring dissolved oxygen concentration, measuring current from each electrode at a second time interval for a third time period, each time is obtained based upon each of the measured currents at which the maximum current is obtained, obtaining each current value within a fourth time period which starts from the time at which the maximum current is obtained, detecting drug sensitivity based upon the variation condition of each current value during the fourth time period. The method allows rapid drug susceptibility measurements.

7 Claims, 5 Drawing Sheets

DRUG SENSITIVITY MEASURING METHOD

CROSS REFERENCE TO RELATED APPLICATIONS

This application is a 371 of PCT/JP01/02198, filed 19 Mar. 2001.

BACKGROUND OF THE INVENTION

1. Technical Field

This invention relates to a drug susceptibility measurement method. In particular, the present invention relates to a method for measuring drug susceptibility using an electrode for detection of dissolved oxygen concentration.

2. Related Art

A prior art method for measuring the susceptibility of bacteria for a drug comprises culturing the bacteria in a solution comprising the drug.

When this method is employed, drug susceptibility is measured by whether or not the bacteria proliferate.

When the above method is employed, drug susceptibility should be measured based upon a turbidity of solution, which increases as proliferation increases. Therefore, the prior art method requires culturing the bacteria for a sufficient time such that turbidity can be judged which is disadvantageous because an extremely long time period (for example, about 18 hours) is needed.

The prior art method is especially disadvantageous in clinical use, because during the long period for measuring drug susceptibility carried out prior to dosage of the drug, the condition of a disease advances and a cure rate is decreased. When a drug is given prior to obtaining the drug susceptibility measurement, resistant bacteria are generated. A powerful drug is required to get rid of the resistant bacteria which increases medical expenses.

The present invention was made in view of the above problems.

It is an object of the present invention to offer a novel drug susceptibility measurement method for rapidly measuring drug susceptibility.

DISCLOSURE OF THE INVENTION

The drug susceptibility measurement method of claim 1 comprises using electrodes for detecting dissolved oxygen concentration within a first compartment or well and a second compartment or well, respectively, the first compartment or well containing solvent of measurement drug solution and the second compartment or well containing drug solution. The method then supplies a microbial suspension of a predetermined concentration to the first and second compartments or wells. The method detects a peak of each signal based upon each signal, each signal being continuously output from each of the electrodes for detection of dissolved oxygen concentration. The method then obtains drug susceptibility based upon the relationship between both signals which are obtained for a predetermined time period starting from the peak timing.

The drug susceptibility measurement method of claim 2 comprises using electrodes for detecting dissolved oxygen concentration within a first compartment or well and a second compartment or well, respectively, the first and second compartments or wells containing a microbial suspension of a predetermined concentration. The method then supplies solvent of measurement drug solution to the first compartment or well and supplies drug solution to the second compartment or well. The method detects a peak of each signal based upon each signal, each signal being continuously output from each of the electrodes for detection of dissolved oxygen concentration. The method then obtains drug susceptibility based upon the relationship between both signals which are obtained for a predetermined time period starting from the peak timing.

The drug susceptibility measurement method of claim 3 corrects both signals so as to determine the peak values of both signals to be previously determined predetermined values. The method then obtains drug susceptibility based upon the relationship between the corrected signals.

The drug susceptibility measurement method of claim 4 employs gradient of each signal as the relationship between signals.

When the drug susceptibility measurement method of claim 1 is employed, a microbial suspension of a predetermined concentration is supplied to the first and second compartments or wells. The method comprises detecting a peak of each signal based upon each signal, each signal being continuously output from each of the electrodes for detection of dissolved oxygen concentration. Then drug susceptibility based upon the relationship between both signals which are obtained for a predetermined time period starting from the peak timing is obtained. Consequently, drug susceptibility can be measured rapidly based upon the signals for a short time period starting from the peak timing. Therefore, in clinical use, treatment can be carried out by rapidly detecting a proper drug (antibiotics etc.). As a result, cure rates are improved and generation of resistant microbe is suppressed.

When the drug susceptibility measurement method of claim 2 is employed, a first drug solution is supplied to the first compartment or well and a second drug solution is supplied to the second compartment or well. The method comprises detecting a peak of each signal based upon each signal, each signal being continuously output from each of the electrodes for detecting dissolved oxygen concentration. Then drug sensitivity based upon the relationship between both signals which are obtained for a predetermined time period starting from the peak timing is obtained. Consequently, drug susceptibility can be measured rapidly based upon the signals for a short time period starting from the peak timing. Therefore, in clinical use, treatment can be carried out by rapidly detecting a proper drug (antibiotics etc.). As a result, cure rates are improved and generation of resistant microbe is suppressed.

When the drug susceptibility measurement method of claim 3 is employed, the method corrects both signals so as to determine the peak values of both signals to be previously determined predetermined values. Then drug susceptibility based upon the relationship between both corrected signals is obtained. Therefore, accuracy in drug susceptibility measurement is improved in addition to the operation and effect of claim 1 or claim 2.

When the drug susceptibility measurement method of claim 4 is employed, the method employs gradient of each signal as the relationship between signals. Therefore, signal processing is simplified improved in addition to the operation and effect of one of claim 1 through claim 3.

BEST MODE FOR CARRYING OUT THE INVENTION

Hereinafter, referring to the attached drawings, we explain a drug susceptibility measurement method according to the present invention in detail.

Figure 1:
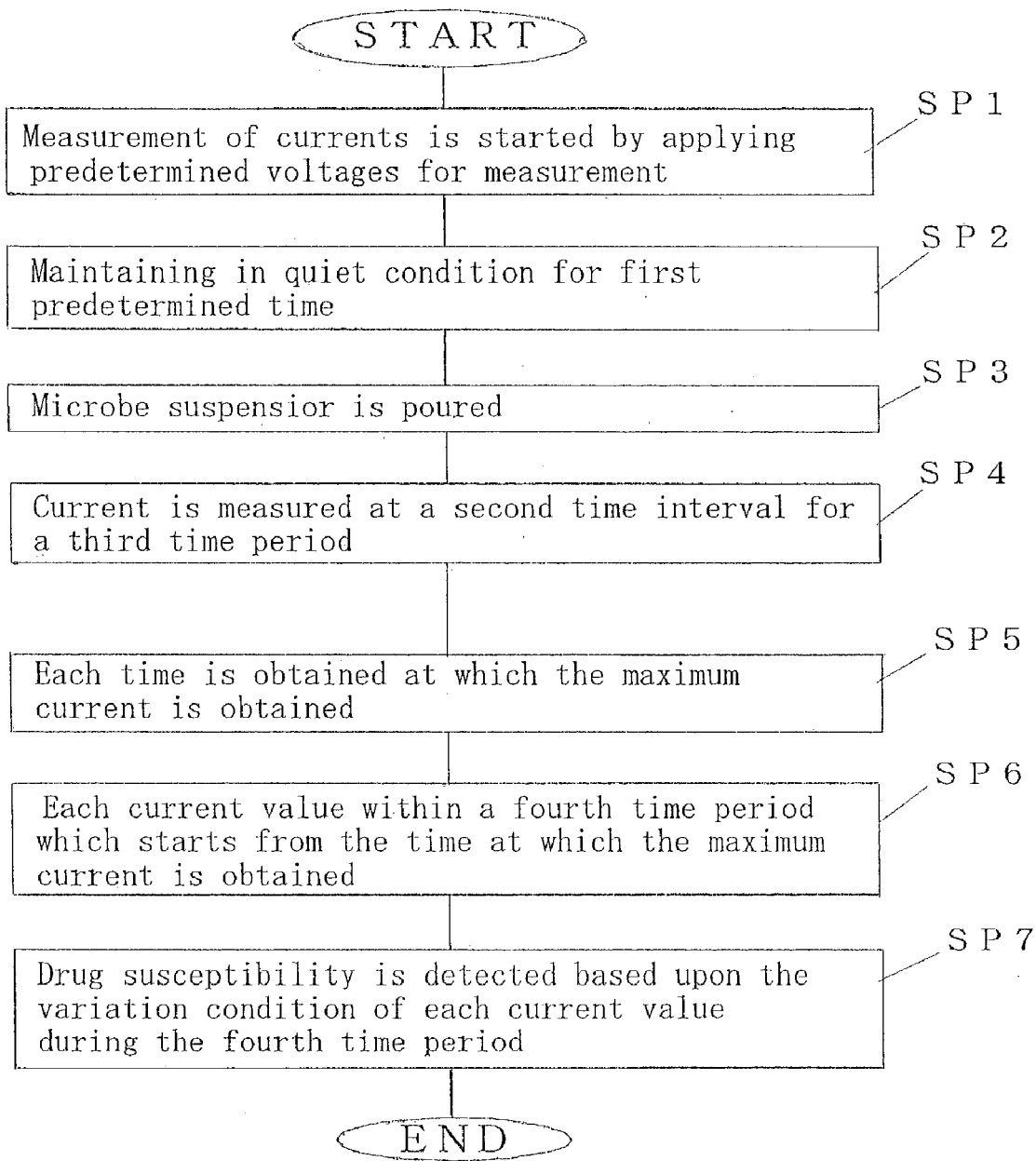
FIG. 1 is a flowchart useful in understanding a drug susceptibility measurement method of an embodiment according to the present invention.

FIG. 1 is a flowchart useful in understanding a drug susceptibility measurement method of an embodiment according to the present invention.

In step SP1, measurement of currents (output signals) is started by applying predetermined voltages to electrodes for measuring dissolved oxygen concentration. The electrodes are provided within a first compartment or well, second compartment or well, and third compartment or well, respectively. The first compartment or well is a compartment or well containing only physiological salt solution. The second compartment or well is a compartment or well containing physiological salt solution and drug solution of a first predetermined concentration. The third compartment or well is a compartment or well containing physiological salt solution and drug solution of a second predetermined concentration. In step SP2, those compartments or wells are kept in a quiet condition for first predetermined time (for t minutes). In step SP3, a microbial suspension is poured into each of the compartments or wells at a position which is in vicinity to the electrode for measuring dissolved oxygen concentration. In step SP4, current from each electrode for measuring dissolved oxygen concentration is measured at a second time interval for a third time period (for example, at every 1 second for 60 seconds). In step SP5, each time is obtained based upon each of the measured currents at which the maximum current is obtained. In step SP6, each current value within a fourth time period which starts from the time at which the maximum current is obtained. In step SP7, drug susceptibility is detected based upon the variation condition of each current value during the fourth time period. Then, the series of operation is finished.

Processing for waiting until a current variation amount for 1 minute becomes equal to or less than a predetermined threshold current (for example, b nA), for example, may be carried out instead the remaining processing in quiet condition for the first predetermined time (for t minutes) which processing is carried out in step SP2. Various factors can be employed as the situation of current variation. It is preferable that a current variation rate is employed for optimization, e.g. simplification in processing.

When the drug susceptibility measurement method corresponding to FIG. 1 is employed, and when a microbial suspension is poured into the first, second and third compartments or wells and dissolved oxygen concentrations are measured, dissolved oxygen concentration within the first compartment or well is decreased following respiration of the microbes. When the microbes are not susceptible to the drug, the dissolved oxygen concentration in all three compartments or wells decrease similarly. When the microbes are susceptible to the drug, the dissolved oxygen concentration in the first compartment or well decreases and the dissolved oxygen concentration in the second and third compartments or wells does not decrease similarly to the first compartment or well, e.g. scarcely decreases. Therefore, the second and third compartments or wells represent the tendency which corresponds to the condition that dissolved oxygen concentration scarcely decreases when the microbes are susceptible to the drug or the condition that dissolved oxygen concentration decreases similarly to the first compartment or well when the microbes are not susceptible to the drug.

This tendency can be judged within a short time period by using electrodes for measuring dissolved oxygen concentration and by using a variation condition of each current value during the fourth time period. Therefore, a required time period for measuring drug susceptibility can be greatly decreased. As a result, the proper drug can be rapidly given so as to improve the cure rate. Further, generation of resistant microbes, such as MRSA or the like, is suppressed so as to reduce medical expenses.

Next, we explain a specific example.

Ampicillin (hereinafter, referred to as ABPC) is employed as the drug solution, and E. coli {2 species of sensitive strain JM109 and resistant strain 5W (ABPC plasmid introduction)} is employed as the microbe.

And, physiological salt solution with its concentration of 0.7% is employed as, the concentration of the ABPC solution is adjusted to be 5.3 µg/ml, and the 2 species of E. coli are adjusted to McFarland2.

The physiological salt solution and the drug solution are contained with the ratio represented in table 1, within the first, second and third compartments or wells. The microbial suspension is contained within syringes each provided in correspondence with each compartment or well.

TABLE 1

|  | Entire amount | species of bacteria | poured bacteria amount | physiological salt solution | drug solution |
|---|---|---|---|---|---|
| Control | 500 µl | JM109 | 40 µl | 500 µl | 0 µl |
|  | 250 µl | JM109 | 20 µl | 250 µl | 0 µl |
| ABPC sensitivity | 500 µl | JM109 | 40 µl | 460 µl | 40 µl |
|  | 250 µl | JM109 | 20 µl | 230 µl | 20 µl |
| ABPC resistance | 500 µl | 5W | 40 µl | 460 µl | 40 µl |
|  | 250 µl | 5W | 20 µl | 230 µl | 20 µl |

Next, the electrode for measuring the dissolved oxygen concentration is mounted to each compartment or well. The first, second and third compartments or wells are maintained quiet condition for 5 minutes so as to make the temperature to be a constant temperature. Syringes containing the microbial suspension are set during the above operation. After the time for maintaining quiet condition has passed, the measurement time is determined to be 360 seconds, and the current from each electrode for measuring the dissolved oxygen concentration is measured at every 0.1 seconds. After 5 minutes (300 seconds) has passed, the microbial suspension is poured into each compartment or well from each syringe rapidly at a constant speed. After the measurement time of 360 seconds has passed, the measured currents are stored and the measured currents are analyzed. This analysis was carried out in the following manner.

The entirety of a series of each of the measured currents is displaced in parallel so as to match the peak point of each series of each of the measured current to the position corresponding to 1.7 seconds. And, figures representing variation characteristic following passage in time are obtained (refer to FIG. 2 representing variation characteristic following passage in time of each of measurement currents when an entire amount is determined to be 0.25 ml, and FIG. 3 representing variation characteristic following passage in time of each of measurement currents when an entire amount is determined to be 0.5 ml).

When theoretical consideration is carried out, at first, microbes determined to be a control, and the sensitive microbes and the resistant microbes are compared. When microbes are resistant microbes, measured current variation characteristic following passage in time which is nearly equal to the control should be obtained because the microbes are scarcely affected by the drug so as to scarcely vary oxygen consumption concentration. On the contrary, when microbes are sensitive microbes, oxygen consumption concentration is decreased, measured current variation characteristic following passage in time should be more gentle with respect to the control, because respiration of the microbes is interfered by the drug.

Figure 2:
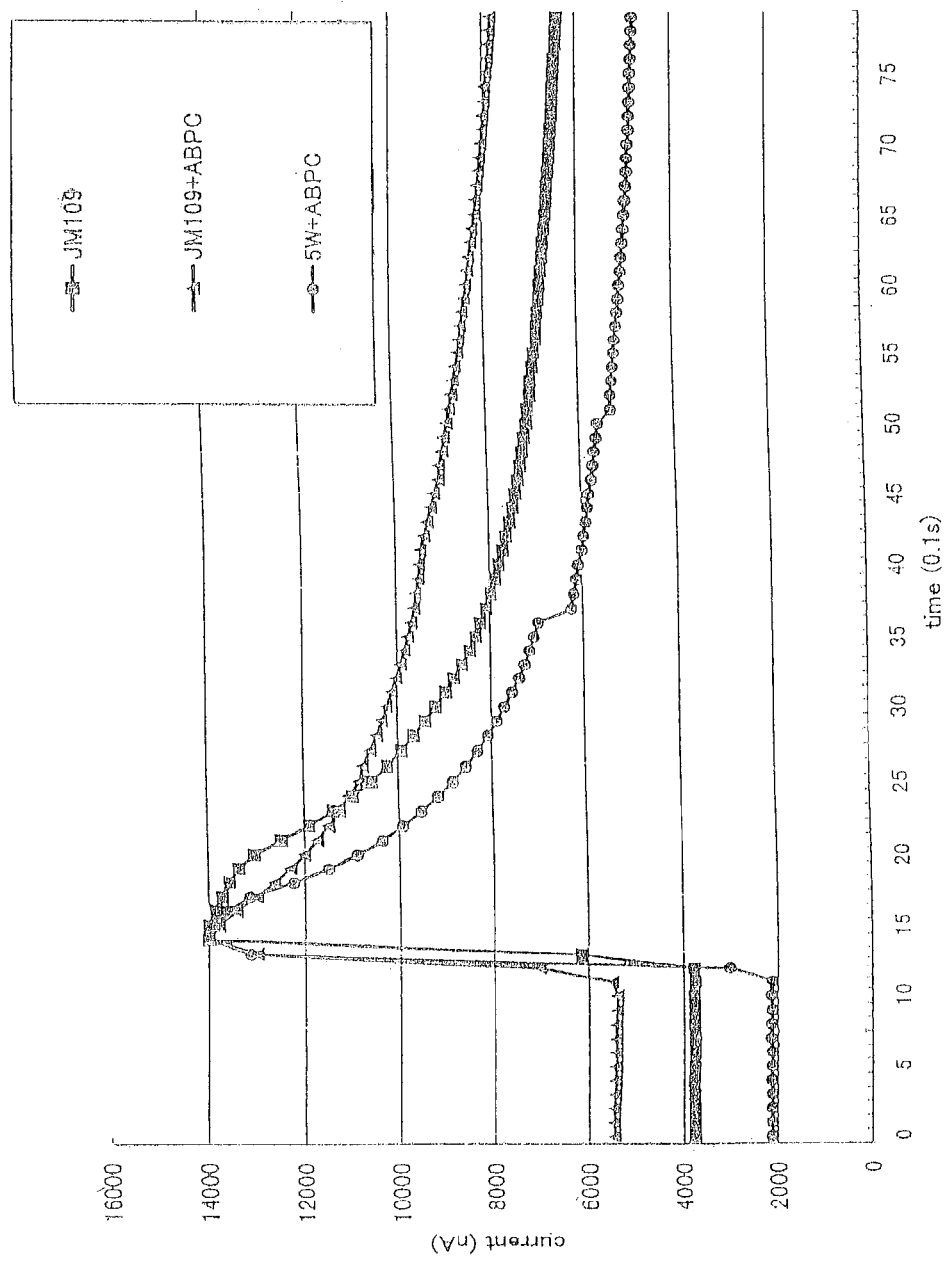
FIG. 2 is a diagram representing variation characteristic following passage in time of each of measurement currents when an entire concentration is determined to be 0.25 ml.
Figure 3:
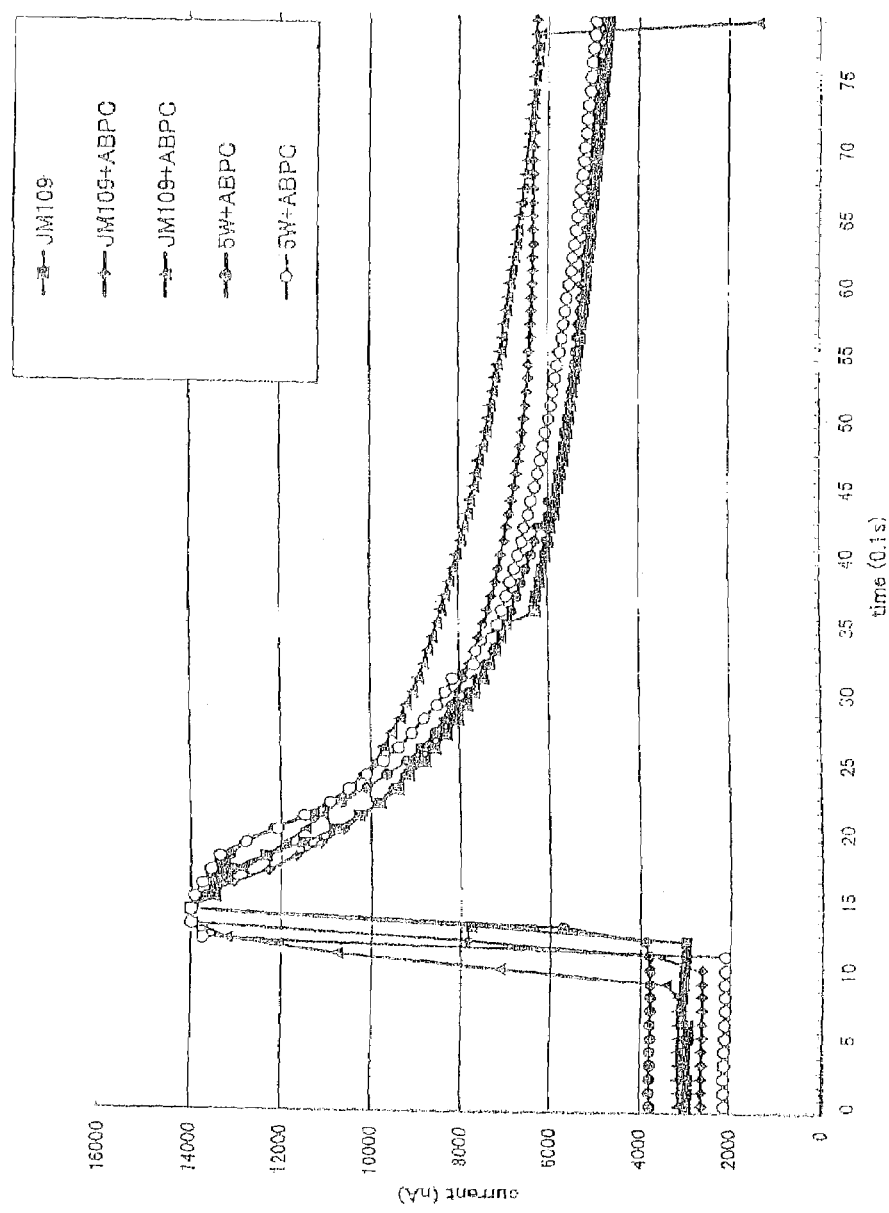
FIG. 3 is a diagram representing variation characteristic following passage in time of each of measurement currents when an entire concentration is determined to be 0.5 ml.

In the actual measurement results illustrated in FIGS. 2 and 3, when sensitive "JM109+ABPC" and resistant "5W+ABPC" are compared by determining the control "JM109" as the reference, the actual measurement results illustrated in FIGS. 2 and 3a represent that a curve corresponding to the sensitive strain is more gentle than curves each corresponding to the control and the resistant strain, and a curve corresponding to the resistant strain is equal to or more steep than the curve corresponding to the control.

Figure 4:
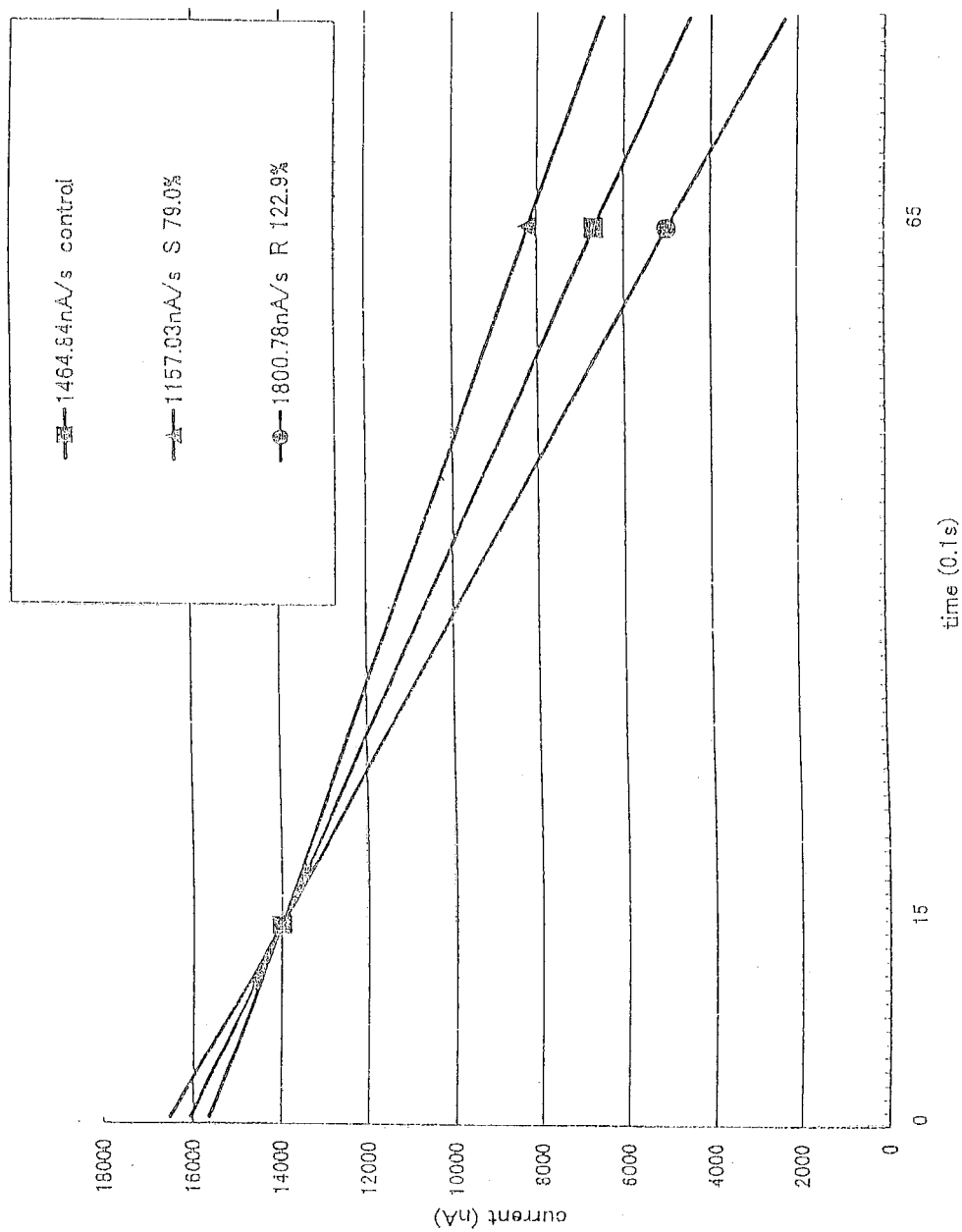
FIG. 4 is a diagram representing gradients of the measurement currents illustrated in FIG. 2.
Figure 5:
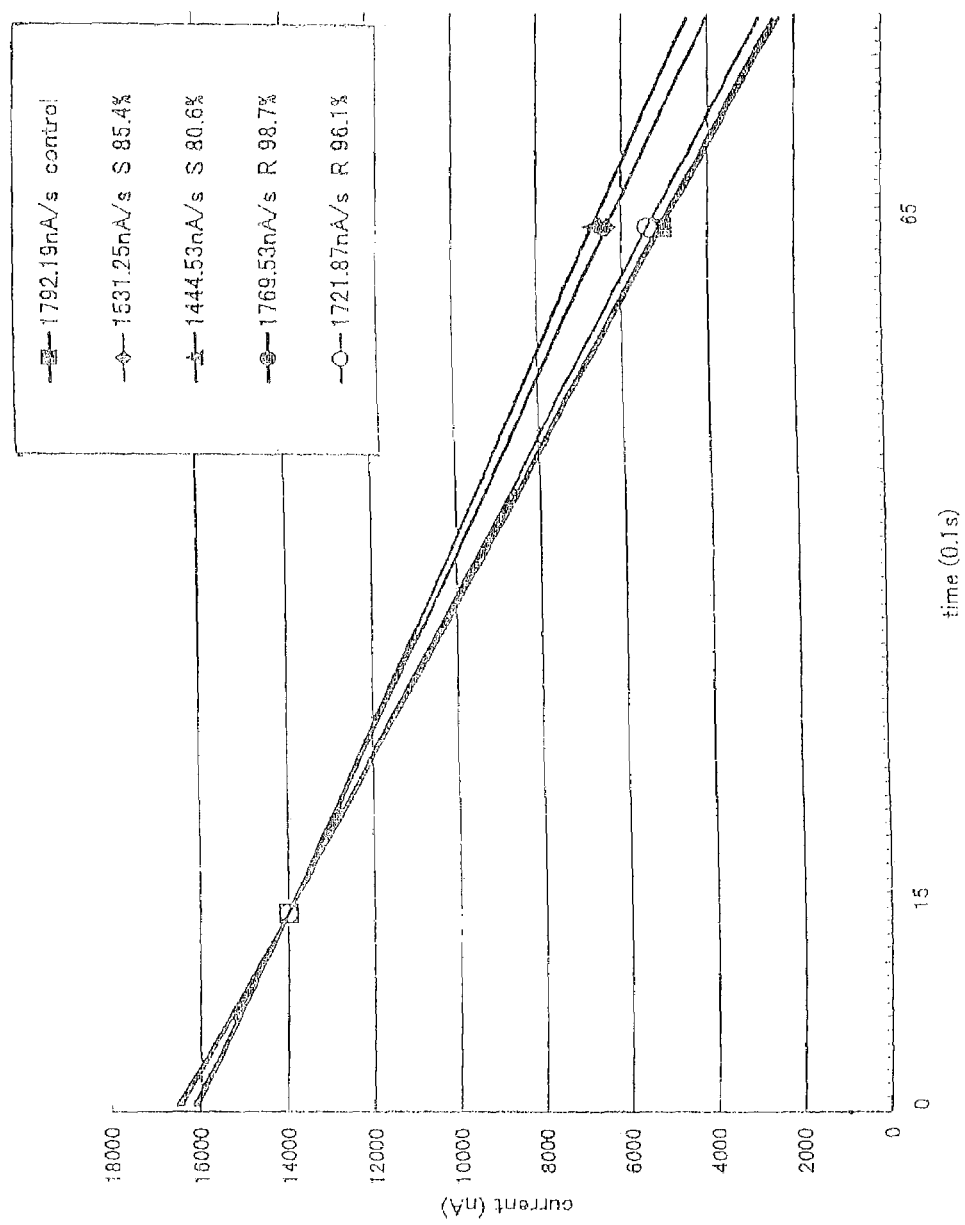
FIG. 5 is a diagram representing gradients of the measurement currents illustrated in FIG. 3.

To digitize the measurement results illustrated in FIGS. 2 and 3, a difference between the current value at the timing 10 seconds having passed from the peak timing and the peak current value is divided by the passage of time so as to obtain the inclination for 10 seconds. As a result, graphs like those illustrated in FIGS. 4 and 5 are obtained.

When each inclination is compared by supposing the inclination corresponding to the control to be 100%, the inclination corresponding to the sensitive strain is 79.0–85.4%, while the inclination corresponding to the resistant strain is 96.1–122.9%.

Therefore, it is sufficient that the threshold value is determined to be 90% when the inclination corresponding to the control is determined to be 100%. A bacterial culture is determined to be a sensitive strain when the inclination is less than 90%. A bacterial culture is determined to be a resistant strain when the inclination is equal to or greater than 90%.

The sensitivity determination may be carried out based upon an inclination for 5 seconds after the peak timing. The sensitivity determination may also be carried out based upon a tendency in measurement current other than the inclination.

The invention of claim 1 has characteristic operation and effect such that drug susceptibility can be measured rapidly based upon the signals for a short time period starting from the peak timing, that treatment can be carried out by rapidly detecting proper drug (antibiotics etc.) in clinical use, and that cure rate is improved and resistant microbe is suppressed in generation.

The invention of claim 2 has characteristic operation and effect such that drug susceptibility can be measured rapidly based upon the signals for a short time period starting from the peak timing, that treatment can be carried out by rapidly detecting proper drug (antibiotics etc.) in clinical use, and that cure rate is improved and resistant microbe is suppressed in generation.

The invention of claim 3 has characteristic operation and effect such that accuracy in drug susceptibility measurement is improved in addition to the operation and effect of claim 1 or claim 2.

The invention of claim 4 has characteristic operation and effect such that signal processing is simplified improved in addition to the operation and effect of one of claim 1 through claim 3.

The invention claimed is:

1. A drug susceptibility measurement method which comprises:
    detecting dissolved oxygen concentration using electrodes within a first compartment or well and a second compartment or well, respectively, the first compartment or well containing a first drug solution and the second compartment or well containing a second drug solution;
    supplying a microbial suspension of a given concentration into the first and second compartments or wells;
    detecting a peak of each signal being continuously output from each of the electrodes; and
    obtaining drug susceptibility based upon a relationship between both signals which are obtained from both compartments or wells for a predetermined time period starting from the peak of each signal.

2. A drug susceptibility measurement method which comprises:
    detecting dissolved oxygen concentration using electrodes within a first compartment or well and a second compartment or well, respectively, the first and second compartments or wells containing a microbial suspension of a given concentration;
    supplying a first drug solution to the first compartment or well and a second drug solution to the second compartment or well;
    detecting a peak of each signal being continuously output from each of the electrodes; and
    obtaining drug susceptibility based upon a relationship between both signals which are obtained from both compartments or wells for a predetermined time period starting from the peak of each signal.

3. The drug susceptibility measurement method as set forth in claim 1, which further comprises correcting both the signals, determining and changing the peak values of both the signals to be previously determined values, and obtaining the drug susceptibility based upon the relationship between both corrected signals.

4. The drug susceptibility measurement method as set forth in claim 1, which further comprises employing the gradient of each signal as the relationship between signals.

5. The drug susceptibility measurement method as set forth in claim 2, which further comprises correcting both the signals, determining and changing the peak values of both the signals to be previously determined values, and obtaining the drug susceptibility on the relationship between both corrected signals.

6. The drug susceptibility measurement method as set forth in claim 2, which further comprises employing the gradient of each signal as the relationship between signals.

7. The drug susceptibility measurement method as set forth in claim 3, which further comprises employing the gradient of each signal as the relationship between signals.

* * * * *